(12) United States Patent
McKee et al.

(10) Patent No.: US 7,115,285 B2
(45) Date of Patent: Oct. 3, 2006

(54) COMPOSITION AND METHOD FOR APPETITE AND CRAVING SUPPRESSION AND MOOD ENHANCEMENT

(75) Inventors: Dwight McKee, Batesville, AR (US); Timothy A. Nolan, Batesville, AR (US)

(73) Assignee: Eurark, LLC, Batesville, AR (US)

( * ) Notice: Subject to any disclaimer, the term of this patent is extended or adjusted under 35 U.S.C. 154(b) by 0 days.

(21) Appl. No.: 10/798,997

(22) Filed: Mar. 12, 2004

(65) Prior Publication Data

US 2004/0198754 A1    Oct. 7, 2004

Related U.S. Application Data

(60) Provisional application No. 60/455,011, filed on Mar. 14, 2003.

(51) Int. Cl.
*A61K 36/00*    (2006.01)
(52) U.S. Cl. .................. 424/725; 514/263.34; 424/729
(58) Field of Classification Search ................ 424/725, 424/729
See application file for complete search history.

(56) References Cited

U.S. PATENT DOCUMENTS

| 5,273,754 | A | 12/1993 | Mann ......................... 424/440 |
| 6,399,089 | B1 | 6/2002 | Yegorova et al. ........... 424/439 |
| 6,565,847 | B1 | 5/2003 | Gorsek ..................... 424/93.45 |
| 2001/0008641 | A1* | 7/2001 | Krotzer ....................... 424/725 |
| 2003/0008048 | A1* | 1/2003 | Winston et al. ............. 426/548 |
| 2004/0005368 | A1* | 1/2004 | Mann et al. ................ 424/725 |

* cited by examiner

*Primary Examiner*—Christopher Tate
*Assistant Examiner*—S. B. McCormick-Ewoldt
(74) *Attorney, Agent, or Firm*—William J. Sapone; Coleman Sudol Sapone P.C.

(57) ABSTRACT

A composition for suppressing appetite and cravings for substances such as nicotine, coffee, sweets or chocolate while improving energy and enhancing mood comprises theobromine or a salt thereof at an effective amount of from about 250 to 4000 mg. Using such relatively high proportions of theobromine, without added caffeine or ephedrine provides an effective method for promoting weight control or to halt substance cravings without the side effects associated with such stimulants. The composition also includes *Rhodiola rosea* extract to offset stress effects from reduced food or substance intake, and to further improve mood, and clarity of thought and ability to handle stress, and to also increase endurance while reducing muscle pain.

6 Claims, No Drawings

COMPOSITION AND METHOD FOR APPETITE AND CRAVING SUPPRESSION AND MOOD ENHANCEMENT

This invention relates to a composition and method for promoting weight control, suppressing cravings for smoking, and addictive substance, for improving mood and for increasing mental clarity.

BACKGROUND

Numerous attempts have been made to provide an oral composition to assist individuals in controlling weight, particularly to improve health. Excess weight can result in a higher incidence of illness, such as diabetes, coronary disease, and a higher risk for certain cancers.

In U.S. Pat. No. 6,447,818, a weight loss composition utilizes ephedrine, or one of its analogs, combined with a Crataegus extract and an extract of Gingko biloba in particular proportions.

In U.S. Pat. No. 6,277,396 a caffeine-ephedrine combination is discussed.

In U.S. Pat. No. 5,543,405, another ephedrine containing composition is discussed.

In U.S. Pat. No. 5,229,390, a dieting composition comprises an amino acid such as arginine, with a stimulant such as caffeine, theophylline or theobromine, and a thiamine type compound in a particular weight ratio.

In U.S. Pat. No. 6,436,946, a composition for oral administration contains caffeine plus a non caffeine stimulant and a cognitive cofactor which ameliorates the diffuse chronic depolarization and subsequent cortical depression commonly associate with stimulants alone.

Many compositions in this area utilize as a stimulant, caffeine and/or ephedrine combined with other ingredients, as stimulants generally suppress appetite, However, these substances have various undesirable side effects. Caffeine increases blood pressure, can cause cardiac arrhythmia, and can give one to have a nervous, jittery feeling. Ephedrine can produce similar side effects and the FDA has recommended that ephedrine not be taken by those with heart disease or high blood pressure. There have been allegations that the misuse of ephedrine containing products has caused several deaths. While ephedrine and/or caffeine compositions may be effective in weight control, the search continues for oral compositions which support weight control without these detrimental side effects.

It is particularly desirable to provide a weight control composition which avoids the "edginess" or "jittery" feeling that often occurs with stimulant use, by avoiding the use of added caffeine or ephedrine.

Various natural based products have been proposed to improve mood, and improve clarity of the thought. For example, U.S. Pat. No. 6,290,994 describes a beverage that contains theobromine or caffeine with vinpocetine citrate for stimulating cerebral activity. U.S. Pat. No. 4,472,387 describes a pharmaceutical composition that increases serotonin concentration which uses a hydroxy tryptophan as a serotonin precursor and a compound such as caffeine or theobromine.

One problem with most weight control compositions is that while they may suppress appetite, they may not reduce the craving for food and in fact, a "rebound" often occurs where, when the stimulant effects wear off, there follows a strong urge to "binge" and overeat, offsetting whatever previous gains have been made.

This craving effect also occurs for those wishing to stop smoking, or other use of tobacco products, or who which to forego an addictive need for specific foods such as coffee or chocolate. No products are known which have a direct effect on such physical cravings.

Consequently, the search continues for natural products that can help an individual with weight control, suppressing appetite as well as cravings for certain foods, such as sweets, for tobacco, chocolate, or other pseudo-addictive substances while improving mood and energy with limited side effects, and particularly for such a product that avoids use of added caffeine and/or ephedrine.

SUMMARY OF THE INVENTION

It is an object of the present invention to provide a composition for oral administration which promotes weight control, by suppressing appetite and cravings while improving mood and promoting clarity of thought, yet avoiding stimulant jitteriness.

It is a further object to provide a composition which is free of ephedrine and avoids the side effects thereof.

It is a further object to provide a composition which is free of added caffeine and avoids the side effects thereof.

It is a further object to provide an oral composition that reduces cravings for food, tobacco smoking and pseudo-addictive substances such as coffee, chocolate, etc.

It is a further object to provide an oral composition which is composed of natural substances, to provide a dietary supplement that is safe and effective.

These and other objects of the present invention are achieved by an oral composition for appetite suppression, craving suppression, weight control and/or mood elevation comprising an effective amount of thcobromine in a physiologically acceptable carrier. Preferably the composition contains from about 250 to 4000 mg. of theobromine or a salt thereof.

The method for achieving appetite suppression, weight control and/or mood elevation comprises orally administrating to a human from 350 to 4000 mg. of theobromine or its salt per day, Preferably, the amount is from about 3–100 mg/kg body weight.

A preferred form of the composition further comprises one or more thermogenic stimulating compositions, to promote fat burning, and optionally an adaptogen such as *Rhodiola rosea* to improve energy, reduce stress and further enhance mood, It has been found that relatively high doses of theobromine are effective in promoting weight control without the side effects associated with caffeine or ephedrine and with further benefits in terms of clarity of thought, mood improvement and energy. These high doses have been also found, surprisingly, to virtually eliminate cravings for tobacco, chocolate or coffee, while limiting the side effects associated with such withdrawal, instead promoting mood improvement, and clarity of thought. Even with some withdrawal effects, such as a headache from caffeine withdrawal, the composition reduces the fatigue and craving that often leads to re addiction.

In a preferred embodiment of the present invention, the high levels of theobromine are combined with *Rhodiola rosea* to produce a particularly synergizing combination that reduces appetite while limiting stress, and producing a calm state that users find particularly beneficial in furthering their weight loss goals.

DETAILED DESCRIPTION OF THE INVENTION

The invention utilizes a methylxanthine compound, specifically theobromine and salts thereof, in relatively high doses, for weight control and mood elevation without the side effects common to caffeine, ephedrine or other stimulants.

Theobromine is an alkaloid, 3,7-dimethylxanthine, resembling caffeine in structure but having different physiological effects. It is typically prepared from the dried ripe seed of theobroma cacao which contains 1–2% of the base, but it can be made synthetically. It may also be produced from natural caffeine by a microbial enzyme process.

The predominant methylxanthine in cocoa beans is theobromine, which derives its name from the latin nomenclature of the cocao tree. Cocoa beans also contain a very small amount of caffeine. Theobromine is also found in smaller quantities in tea, and the South American stimulating herb known as Yerba maté, but it is found in greatest amounts in cocoa and chocolate. Theobromine has only one-tenth the stimulant activity of caffeine, but has subtle and sustained effects in support of healthy mood, energy, and appetite. Like the other methylxanthines, it is also thermogenic, meaning that it supports burning of calories to produce heat. Like caffeine and theophylline, the predominant methylxanthine in tea, theobromine inhibits the enzyme that breaks down cyclic adenosine monophosphate (cAMP), thus increasing availability of this high-energy compound that acts on receptors in many cells of the body, including fat and muscle cells. This is believed to be one of the primary mechanisms by which theobromine supports an increase in metabolic rate and the stimulation of fat breakdown (lipolysis).

Theobromine or its salts are present in various compositions at relatively low levels. Theobromine has been used as a diuretic, stimulant, bronchodialater and cardiotonic.

However, it has not been used as a weight-control agent, generally limited to being a secondary ingredient present at relatively low levels of about 1–200 mg. which are believed to be essentially inactive.

It was recently discovered that rather high doses of theobromine, "high" meaning over 250 mg. per day, preferably over 1000 mg. per day, has significant effectiveness in suppressing appetite, on its own, and without secondary compounds such as ephedrine or caffeine, yet this effectiveness is achieved without the common side effects associated with comparable high doses of caffeine. In fact, additional unexpected benefits are achieved in a general mood elevation and improved energy. It was further discovered that the high doses of theobromine reduce or eliminate cravings for substances such as nicotine from tobacco smoking, as well as for coffee, sweets, and chocolate.

In the inventive composition, theobromine or its salts can be used. The salts of theobromine may include those with calcium, sodium, lithium, potassium, magnesium, etc., though other salts can likely also be used. Theobromine and its salts are available in relatively pure form as either extracts, by synthesis or by other means.

In a preferred embodiment, the composition optimally contains one or more of cacao, or cinnamon bark which are believed to work synergetically with theobromine to suppress appetite and improve mood.

Cinnamon is a widely used spice, also known to be rich in antioxidant polyphenols, particularly procyanidin dimers and oligomers (OPCs). One of the polyphenols, in cinnamon, known as methylhydroxy chalcone polymer, has been found to have particularly strong activity in the support of healthy blood sugar levels. Blood sugar that is too high or too low can cause fatigue, mood swings, irritability, and hunger. Stabilizing blood sugar levels is important in reducing craving for sweets and other refined carbohydrates, that can cripple an individual's weight loss program.

The composition can include various optional ingredients that complement or support the weight control, substance cravings and appetite, and mood enhancing properties of the invention, or which support health in general. In particular, the use of the inventive composition has reduced the craving to smoke, while at the same time suppressing appetite, so that those wishing to stop smoking can do so without the normal weight gain often encountered by those who quit smoking.

Other optional ingredients may include, but are not limited to compounds such as various antioxidants, vitamins, minerals, fiber, memory promoters, nutritional supplements, and herbal supplements. These may include but are not limited to: green tea, Yerba mate, cocoa, guarana seed, *Citrus aurantium*, Damiana (leaf, stem), *Schizonopeta* spica, Kola nut, *Coleus forskohli, Panax* ginseng, *Rhodiola kirilowli* (Tibetan ginseng), Ginger root, defatted Jojoba meal (*Simmondsia chinensis*), and extracts of any of the above, provided these do not detract from or degrade the beneficial properties of theobromine. More specifically, chromium pyruvate, chromium sulfate, chromium chloride, chromium aspartate, chromium picolinate, chromium polynicotinate, or other salts, chromium enriched yeast, vitamin C, bioflavanoids, oligomeric proanthocyanadins, various polyphenols, coenzyme QI0, L-carnitine, acetyl-L-carm tine, choline, amino acids, vitamin B2 and B6, zinc, etc., may be used as these may contribute beneficial attributes to suppress appetite, support weight control or fat burning and enhance mood.

One preferred ingredient is trace chromium which is important to the healthy regulation of blood sugar. It is an essential mineral found in a concentration of about 20 parts per billion in the blood. Chromium supports the activity of certain enzymes which help in the utilization of glucose and the synthesis of essential lipids in the body. It is necessary for the proper activity of insulin in its function of moving glucose from the blood into cells. This mineral may also be involved in the synthesis of protein through its binding action with RNA molecules. Chromium is poorly absorbed from the intestinal tract. Only 3% of dietary intake is retained. Excretion occurs mainly through the urine. The amount of chromium stored in the body decreases with age. Diets high in sugars and other refined carbohydrates increase utilization and excretion of chromium from the body.

A preferred combination is theobromine with a *Rhodiola* extract, particularly, *Rhodiola rosea* extract, generally obtained in the form of a dry powder containing cinnatrol alcohol glycosides in particular rosarins, rosins, rosavins and/or salidrosides.

*Rhodiola rosea* has been part of traditional healing systems in Asia since the time of Chinese emperors, who sent expeditions to Siberia to obtain it. The Vikings were reported to have used the herb to enhance their endurance, physical, and mental strength. Research has revealed that the roots of this plant contain powerful adaptogens—defined as substances that nonspecifically increase resistance to physical, mental, emotional, toxic, or environmental stress, without disturbing normal biological measurements or functions.

Key to the activity of the *Rhodiola rosea* extract is its ability to activate the enzyme called hormone sensitive lipase. This enzyme is activated by exercise, and normally requires at least an hour of moderate exercise, such as brisk walking, to be activated—after which its activity persists for about 12 hours. Soviet clinical studies have shown that the combination of *Rhodiola rosea* extract together with physical exercise can be a powerful tool in the activation of this lipase enzyme, resulting in enhanced breakdown of stored fat. A clinical trial done in Bulgaria randomized 121 subjects to either *Rhodiola rosea* extract or a placebo, and tested serum free fatty acid levels at rest, and after one hour of exercise. The *Rhodiola* group had a 6% greater serum fatty acid level at rest, and a 44% greater level after exercise, indicating increased activation of lipase (triglyceride catabolizing enzyme) by the combination of *Rhodiola* and exercise vs exercise alone. The extract also has shown synergy with calorie restricted diet—another placebo controlled clinical study done at the Georgian State Hospital in the former Soviet Union with 130 obese patients who all walked for 30 minutes after each meal showed that the intake of tablets of *R. rosea* extract led to a mean weight loss of 19 pounds (11% reduction of body fat), compared to only an 8 pound loss by the placebo group on exactly the same diet.

Because theobromine also activates lipolysis and thermogenesis, the combination of these phytonutrients, along with cinnamon and chromium, provides a well balanced composition to promote weight loss by suppressing appetite and reducing fat while minimizing side effects and in particular stress effects often associated with dieting.

While *Rhodiola rosea* has been shown to activate honnone sensitive lipase to assist in the breakdown of stored fat, a complement to theobromine, it is also an adaptogen, which is a compound that increases overall resistance to a variety of chemical, biological and physical stress agents. In particular, it has been shown to improve energy and physical fitness by increasing blood flow to the muscles and brain, also reducing mental fatigue. It thus can significantly offset the stress induced on the body through reduced food intake and during the reduction of body fat and promote a general sense of well being. Also, increasing basic metabolism while reducing stress promotes immune stimulation.

The reduction in cravings for substances such as tobacco, derived from administration of high doses of theobromine, is also synergisticly supported by the addition of *Rhodiola rosea*, since the stresses associate with withdrawal are believed ameliorated by *Rhodiola rosea*, increasing the effectiveness in preventing cravings for nicotine. Thus, suppression of appetite, as well as for smoking or cravings for other substances are reduces, while a calm mood and clearer thinking ease the transition to non-addictive behavior.

In particular, a composition containing from 50–1200 mg. of *Rhodiola rosea* together with from 250–4000 mg. of theobromine provides a well balanced, caffeine and ephedrine free composition for supporting weight control suppressive appetite and substance cravings, and improving mood and mental function.

The method for controlling weight and substance intake and improving mental function and mood comprises orally administering a composition containing from 250 to 4000 mg. of theobromine, and from 10–600 mg. of *Rhodiola rosea* to a person in need of such treatment.

In using the composition of the invention for weight control or for suppressing substance cravings and improved cerebral function, the dose may vary widely depending upon the route of administration, the condition, body weight, age and sex of a person, the judgment of a physician treating the person, etc. Generally, in administration to humans, the doses for theobromine are 3.0 mg/kg/day to 100 mg/kg/day, preferably 5.0 mg/kg/day to 80 mg/kg/day, more preferably 20 mg/kg/day to 50 mg/kg/day, either at one time or in several divided portions daily. The doses for *Rhodiola rosea* are from 0–20 mg/kg/day, preferably 0–10 mg/kg/day.

The route of administration is preferably oral but may be parenteral (e.g. intravenous, intraarterial, intramuscular, intraperitoneal, intramedullary, intrarectal), or transdermal. For administration, the composition may be formulated into forms suitable for the above routs of administration, for example forms suitable for oral administration such as tablets, granules, powders, coated tablets, hard capsules, elastic capsules and syrups, or forms suitable for injection or intravenous drip infusion such as suspension, solutions, or oily or aqueous emulsions.

Adjuvants normally used in formulating medicaments in the above-exemplified forms may equally be used with the inventive composition, such as pharmaceutically acceptable liquid or solid diluents or carriers for formulating the compositions of this invention. Specific examples include syrup, gum Arabic, gelatin, sorbitol, tragacanth, polyvinyl pyrrolidone, magnesium stearate, talc, polyethylene glycol, silica, lactose, sucrose, corn starch, calcium phosphate, glycine, potato starch, carboxymethyl cellulose calcium, sodium laurylsulfate, water, ethanol, glycerol, mannitol, and a phosphate buffer, among others.

The composition of this invention may, if required, further contain other adjuvants customarily used in the field of phannaceutical formulation, such as coloring agents, flavors, corrigents, antiseptics, dissolution acids, suspending agents and dispersing agents.

The composition may be in unit dosage forms such as tablets, capsules, coated tablets and ampoules mentioned above, or may be in a form contained in a multi-dosage receptacle.

The composition, depending upon its form, etc., may contain the active ingredients of the invention in a concentration of generally 0.10 to 50% by weight.

The only caution, as with any dietary supplement, is that it is prudent that it should not be used by pregnant or lactating women, by persons suffering from chronic illness, bipolar disorder, or taking prescription medicine, including oral contraceptives, etc., without consulting a health care professional.

The inventive composition has additional advantages. By containing natural diuretics and mood enhancing ingredients, it is useful in the treatment of premenstrual syndrome, particularly when both theobromine and *Rhodiola rosea* are present, as this provides additional relief from stress. It has also been found to reduce muscle pain from exercise, as an adjunct to the increased physical endurance obtainable from the use of *Rhodiola rosea*, and so may be used by those not necessarily seeking weight loss but as a natural aide for sports, exercise and physical labor or other activity where muscle pain is present.

The term "added caffeine" means that some residual caffeine may be present in the composition, such as in cocao powder but no separate caffeine is added and in any event, no more than about 1 mg. of caffeine should be present in the inventive composition.

The extracts used in the inventive composition are preferably manufactured to high quality standards, and are documented as being safe through historical use and/or laboratory tests.

The term "dose" as used herein means physically discrete units suitable as unitary dosages for human consumption, each unit containing a predetermined quantity of the composition believed to produce the desired therapeutic effect, in association with a physiologically tolerable carrier, diluent or vehicle.

The following lists one exemplary tablet or capsule composition, with possible ranges of these ingredients, according to the invention:

Per tablet, (recommended 3–6 tablets per day)

|  | Basic | Preferred |
| --- | --- | --- |
| Theobromine | 250–1250 mg. | 250–750 mg. |
| Cocoa | 0–80 Mg. | 20–80 mg. |
| Cinnamon Bark Powder | 0–80 mg. | 20–80 mg. |
| Base | 1–5 mg. | 2.5 mg. |
| Papain | 0–1 Mg. | 0.5 mg. |
| Bromelain | 0–2 mg. | 0.5 mg. |
| Chromium sulphate | 0–250 mcg. | 60–150 mcg. |
| Rhodiola rosea | 0–1200 mg. | 50–600 mg. |

Theobromine

A 25 year old woman took 500 mg. of theobromine, 4 times per day for 21 days, 2,250 mg. tablets in the morning and 2, 250 mg. tablets at lunch. She reported reduced appetite and food cravings and increased energy without a stimulant high. She lost 8 lbs. and reported no side effect.

A 18 year old woman took 4, 250 mg. tablets of theobromine four times per day, for 21 days. She reported having an elevated mood, more energy and reduced appetite. She lost 18 lbs., and did report having a headache. No other side effects were reported.

A 48 year old woman took 3, 250 mg. tablets of theobromine per day for 10 days. She reported excellent energy, reduced appetite and a euphoric calmness to her mood. She lost 8 lbs. and only experienced slight dizziness one day. No other side effects were reported.

A 45 year old man took up to 2 grams daily of theobromine tablets for 28 days. He reported lowered appetite and no energy or mood difference and no side effects. He lost 9 lbs. in 21 days.

A 50 year old man took 2 grams of theobromine per day, for 12 days. He reported less appetite, more energy, improved mood and clearer thinking. No side effects were reported other than increased water intake. He had a 5 pound weight loss.

A 60 year old woman who had been pseud-o-addicted to sweets and had cravings for sweets all her life, took one 250 mg. tablet of theobromine per day and reported no craving for such sweets thereafter.

A 59 year old woman used Dexatrim (phenylpropanolamine) for about 3 weeks, and reported appetite suppression for only one week and was jittery, energy early, but low energy and fatigue later in the day. She also took Metabolife 356® made by Metabolife International Inc. which contains a caffeine-ephedrine combination. She did report suppressed appetite but had feelings of nervousness and disorientation. She then took 500 mg. of Theobromine, and reported good energy, appetite suppression, with no nervous or jittery sensation. Instead she felt a sense of well being.

A 42 year old woman had been taking Xenadrine EFX (ephedrine free, contains synephrine) to try to stop smoking while losing weight, but with little effect on her appetite and nicotine craving. Upon switching to 750 mg. theobromine per day, for three weeks, she reported a loss of the urge to smoke as well as reduced appetite, and also a reduction in cravings for chocolate prior to her menses, which had always occurred. She reported feeling much calmer and less angry. She discontinued use of theobromine over a weekend, and noted that the urge to smoke again became strong. When she re-started theobromine after the weekend, the urge to smoke had dissipated by the end of the day. She was also exercising, and despite quitting smoking at the same time, lost 4.5 pounds, and reported fitting into clothes that she hadn't been able to wear for several years.

While preferred embodiments of the present invention have been shown and described, it will be understood by those skilled in the art that various changes or modifications can be made without varying from the present invention.

What is claimed is:

1. A composition for suppressing appetite and substance cravings including cravings for nicotine, sweets, and chocolate, while improving mood and energy comprising as active ingredients, effective amounts of theobromine or a salt thereof, the theobromine or its salt being present at from 250 to 4000 mg., cocoa present at from 20–80 mg., cinnamon bark powder present at from 20–80 mg., an extract of *Rhodiola rosea* present at from about 50–1200 mg., elemental chromium present at from 25–500 mcg., and a pharmaceutically acceptable carrier, wherein the composition total active ingredient weight is from 340 to 5360 mg.

2. The composition of claim 1 wherein the effective amount of theobromine or a salt thereof is from about 250 to 2000 mg.

3. The composition of claim 1 further comprising a compound selected from the group consisting of antioxidants, vitamins, minerals, fiber, chromium pyruvate, chromium sulfate, bioflavanoids, polyphenols, amino acids, memory promoters, nutrional supplements, herbal supplements, green tea, green tea extract, Yerba mate, Yerba mate extract, cocoa, cocoa extract, guarana seed, guarana seed extract, *Citrus aurantium, Citrus aurantium* extract, Damiana, Damiana extract, *Schizonopeta* spica, *Schizonopeta* spica extract, Kola nut, Kola nut extract, *Coleus forskohli, Coleus forskohli* extract, *Panax* ginseng, *Panax* ginseng extract, *Rhodiola kirilowii, Rhodiola kirilowii, Rhodiola kirilowii* extract, Ginger root, Ginger root extract, defatted Jojoba meal (*Simmondsia chinensis*), Jojoba meal extract, coenzyme Q10, L-carnitine, Acetyl-L-carnitine, choline, and combinations thereof.

4. The composition of claim 1 wherein the salts of theobromine are calcium, sodium, potassium, lithium, magnesium salts or combination thereof.

5. The composition of claim 1 wherein the chromium is selected from the group consisting of chromium sulfate, chloride, aspartate, picolinate, or polynicotinate and combinations thereof.

6. The composition of claim 1 wherein the composition is in the form selected from the group consisting of tablets, granules, powders, coated tablets, capsules, syrups, suspensions, solutions and emulsions.

* * * * *